United States Patent [19]

O'Riordan et al.

[11] Patent Number: 5,939,536
[45] Date of Patent: Aug. 17, 1999

[54] METHODS FOR PURIFYING CYSTIC FIBROSIS TRANSMEMBRANE CONDUCTANCE REGULATION

[75] Inventors: Catherine R. O'Riordan, Boston; Amy L. Helgerson (Erickson), Charlton, both of Mass.

[73] Assignee: Genzyme Corporation, Framingham, Mass.

[21] Appl. No.: 08/785,107

[22] Filed: Jan. 21, 1997

Related U.S. Application Data

[63] Continuation-in-part of application No. 08/118,054, Sep. 8, 1993, abandoned, which is a continuation-in-part of application No. 08/114,950, Aug. 27, 1993, abandoned, which is a continuation-in-part of application No. 08/087,132, Jul. 2, 1993, which is a continuation of application No. 07/613,592, Nov. 15, 1990, abandoned, which is a continuation-in-part of application No. 07/589,295, Sep. 27, 1990, abandoned, which is a continuation-in-part of application No. 07/488,307, Mar. 5, 1990, abandoned.

[51] Int. Cl.$^6$ .................................................. C07K 14/00
[52] U.S. Cl. ........................................... 530/413; 530/350
[58] Field of Search ....................................... 530/413, 350

[56] References Cited

U.S. PATENT DOCUMENTS

| | | | |
|---|---|---|---|
| 5,215,963 | 6/1993 | Feldman et al. | 514/8 |
| 5,240,846 | 8/1993 | Collins et al. | 435/240.1 |

FOREIGN PATENT DOCUMENTS

| | | |
|---|---|---|
| WO 91/02796 | 8/1990 | WIPO. |
| WO 91/10734 | 1/1991 | WIPO. |

OTHER PUBLICATIONS

C. Mundina–Weilenmann et al., "Demonstration of the Phosphorylation of Dihydropyridine–sensitive Calcium Channels in Chick Skeletal Muscle and the Resultand Activation of the Channels after Reconstitution", *The Journal of Biological Chemistry*, 266, 1991, pp. 4067–4073.

S. Dunn et al., "Functional Reconstitution of the Bovine Brain GABA$_A$ Receptor from Solubilized Components", *Biochemistry*, 28, 1989, pp. 2545–2551.

P. Jezek et al., "Reconstitution of the Beef Heart and Rat Liver Mitochondrial K$^+$/H$^+$ (Na$^+$/H$^+$) Antiporter", *The Journal of Biological Chemistry*, 265, 1990, pp. 10522–10526.

J. Zhang et al., "Characterization of the V$_o$ Domain of the Coated Vesicle (H$^+$)–ATPase", *The Journal of Biological Chemistry*, 267, 1992, pp. 9773–9778.

Scopes, R.K., *Protein Purification, Principles and Practice*, 1982, pp. 30–157, Springer–Verlag.

Ward, J.M., et al. "Proton Transport Activity of the Purified Vacuolar H$^+$–ATPase for Oats$^{1}$", *Plant Physiology*, 99, 1992, pp. 925–931.

Denning, G.M., et al., "Processing of mutant cystic fibrosis transmembrane conductance regulator is temperature–sensitive", *Nature*, 358, 1992, pp. 761–764.

Clari G., et al., "Comparative characterization of membrane–associated and cytosolic Tyr–protein kinases in human erythrocytes", *European Journal of Biochemistry*, 179, 1989, pp. 581–588.

Cheng, S.H. et al., "Defective Intracellular Processing of CFTR as the Molecular Basis of Cystic Fibrosis", *Cystic–Fibrosis Current Topics*, 1, 1993, pp. 175–189.

Teem, J.L. et al., "Identification of Revertants for the Cystic Fibrosis ΔF508 Mutation Using STE6–CFTR Chimeras in yeast", *Cell*, 73, 1993, pp. 335–346.

Welsh, M.J. and Smith, A.E., "Molecular Mechanisms of CFTR Chloride Channel Dysfunction in Cystic Fibrosis", *Cell*, 73, 1993, pp. 1251–1254.

DiTullio, P. et al., "Production of Cystic Fibrosis Transmembrane Conductance Regulator in the Milk of Transgenic Mice", *Bio/Technology*, 10, 1992, pp. 74–77.

Rosenfeld, M.A. et al., "In Vivo Transfer of the Human Cystic Fibrosis Transmembrane Conductance Regulator Gene to the Airway Epithelium", *Cell*, 68, 1992, pp. 143–155.

Thomas, P.J. et al., "The Cystic Fibrosis Transmembrane Conductance Regulator", *Journal of Biological Chemistry*, 267(9), 1992, pp. 5727–5730.

Welsh, M.J. et al., "Cystic Fibrosis Transmembrane Conductance Regulator: A Chloride Channel with Novel Regulation", *Neuron*, 8, 1992, pp. 821–829.

Kartner, N. et al., "Mislocalization of ΔF508 CFTR in Cystic Fibrosis Sweat Gland", *Nature Genetics*, 1, 1992, pp. 321–327.

Bear, C.E. et al., "Purification and Functional Reconstitution of the Cystic Fibrosis Transmembrane Conductance Regulator", *Cell*, 68, 1992, pp. 809–818.

Ostegaard, L.S. and Welsh, M.J., "Partial Purification of the Cystic Fibrosis Transmembrane Conductance Regulator", *Journal of Biological Chemistry*, 267(36), 1992, pp. 26142–26149.

Smith, A.E., "Emerging Therapies for Cystic Fibrosis", Section V—Topics in Biology, *Ann. Rep. Med. Chem.*, 27, 1992, pp. 235–243.

Tilly, B.C. et al., "Cyclic AMP–Dependent Protein Kinase Activation of Cystic Fibrosis Transmembrane Conductance Regulator Chloride Channels in Planar Lipid Bilayers", *Journal of Biological Chemistry*, 267(14), 1992, pp. 9470–9473.

Denning, G.M. et al., "Localization of Cystic Fibrosis Transmembrane Conductance Regulator in Chloride Secretory Epithelia", *J. Clin. Invest.*, 89, 1992, pp. 339–349.

(List continued on next page.)

Primary Examiner—Karen C. Carlson

[57] ABSTRACT

The present invention provides a method for purifying a membrane associated protein, e.g., cystic fibrosis transmembrane conductance regulator (hereinafter CFTR) in a functional form. The method involves contacting a membrane-associated protein-membrane fraction complex with a detergent forming a solubilized complex and chromatographically isolating the membrane-associated protein from the solubilized complex in a functional form. The functional form of the purified membrane-associated protein of the present invention preferably is sufficiently pure to allow its introduction into humans for therapeutic purposes.

4 Claims, 1 Drawing Sheet

OTHER PUBLICATIONS

Sarkadi, B. et al., "Biochemical Characterization of the Cystic Fibrosis Transmembrane Conductance Regulator in Normal and Cystic Fibrosis Epithelial Cells", *Journal of Biological Chemistry*, 267, 1992, pp. 2087–2095.

Kartner, N. et al., "Expression of the Cystic Fibrosis Gene in Non–Epithelial Invertebrate Cells Produces a Regulated Anion Conductance", *Cell*, 64, 1991, pp. 681–691.

Rosenfeld, M.A. et al., "In Vivo Transfer of the Human Cystic Fibrosis Gene to the Respiratory Epithelium", *Clin. Res.*, 39(2), 1991, p. 311A.

Gregory, R.J. et al., "Expression and Characterization of the Cystic Fibrosis Transmembrane Conductance Regulator", *Nature*, 347, 1990, pp. 382–386.

Rich, D.P. et al., "Expression of the Cystic Fibrosis Transmembrane Conductance Regulator Corrects Defective Chloride Channel Regulation in Cystic Fibrosis Airway Epithelial Cells", *Nature*, 347, 1990, pp. 358–363.

Riordan, J.R. et al., "Identification of the Cystic Fibrosis Gene: Cloning and Characterization of Complementary DNA", *Science*, 245, 1989, pp. 1066–1073.

Rommens, J.H. et al., "Identification of the Cystic Fibrosis Gene: Chromosome Walking and Jumping", *Science*, 245, 1989, pp. 1059–1065.

Kerem, B.S. et al., "Identification of the Cystic Fibrosis Gene: Genetic Analysis", *Science*, 245, 1989, pp. 1073–1080.

O'Riordan, C. et al., "Purification and Characterization of Recombinant Cystic Fibrosis Transmembrane Conductance Regulator", *Journal of Biological Chemistry*, 270, 1995, pp. 17033–17043.

METHODS FOR PURIFYING CYSTIC FIBROSIS TRANSMEMBRANE CONDUCTANCE REGULATION

RELATED APPLICATIONS

The present application is a continuation-in-part of U.S. Ser. No. 08/118,054 filed on Sep. 8, 1993, now abandoned, itself a continuation-in-part application of U.S. Ser. No. 08/114,950 filed on Aug. 27, 1993, now abandoned, which is a continuation-in-part of U.S. Ser. No. 08/087,132, filed Jul. 2, 1993, which is a continuation application of U.S. Ser. No. 07/613,592, filed Nov. 15, 1990 and now abandoned, which is in turn a continuation-in-part application of U.S. Ser. No. 07/589,295, filed Sep. 27, 1990 and now abandoned, which is a continuation-in-part application of U.S. Ser. No. 07/488,307, filed Mar. 5, 1990 and now abandoned. This application is also related to the subject matter described in co-pending application U.S. Ser. No. 07/985,478 filed Dec. 2, 1992 now abandoned. The contents of all of the above co-pending patent applications are incorporated herein by reference. Definitions of language or terms not provided in the present application are the same as those set forth in the co-pending applications. Any reagents or materials used in the examples of the present application whose source is not expressly identified also is the same as those described in the copending applications, e.g., F508 CFTR gene and CFTR antibodies.

BACKGROUND OF THE INVENTION

Cystic Fibrosis (CF) is the most common fatal genetic disease in humans (Boat, T. et al. Cystic fibrosis. In: *The Metabolic Basis of Inherited Disease,* C. Scriver, A. Beaudet, W. Sly, and D. Valle, eds. (McGraw Hill, New York, 1989), 2649–2860). Based on both genetic and molecular analysis, a gene associated with CF was isolated as part of 21 individual cDNA clones and its protein product predicted (Kerem, B-S. et al. *Science* 245:1073–1080 (1989); Riordan, J. et al. *Science* 245:1066–1073 (1989); Rommens, J. H. et al. *Science* 245:1059–1065 (1989)).

U.S. Ser. No. 07/488,307 describes the construction of the gene into a continuous strand, expression of the gene as a functional protein and confirmation that mutations of the gene are responsible for CF. (See also Gregory, R. J. et al. *Nature* 347:382–386 (1990); Rich, D. P. et al. *Nature* 347:358–363 (1990)). The co-pending patent application also discloses experiments which showed that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan, J. et al. *Science* 245:1066–1073 (1989)). CFTR is a protein of approximately 1480 amino acids made up of two repeated elements, each having six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistant (MDR) P-glycoprotein, bovine adenyl cyclase, the yeast STE6 protein as well as several bacterial amino acid transport proteins (Riordan, J. et al. *Science* 245:1066–1073 (1989); Hyde, S. C. et al. *Nature* 346:362–365 (1990). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. et al. *Science* 245:1066–1073 (1989); Frizzell, R. A. et al. *Science* 233:558–560 (1986); Welsh, M. J. and Liedtke, C. M. *Nature* 322:467 (1986); Li, M. et al. *Nature* 331:358–360 (1988); Hwang, T-C. et al. *Science* 244;1351–1353 (1989); Li, M. et al. *Science* 244:1353–1356 (1989)). Difficulties can be encountered when attempting to purify CFTR or other membrane-associated proteins because a purification process may not result in a functional protein.

Additional Information Concerning Glycosylation of CFTR

CFTR is a membrane-associated glycoprotein that can be phosphorylated in vitro (Gregory et al., 1990, "Expression and characterization of the Cystic Fibrosis transmembrane conductance regulator", *Nature,* 347, pp. 382–386). The protein has a primary translation product which migrates with apparent molecular weight on SDS-polyacrylamide gels of 130k (referred to as band A). In vaccinia virus-infected, cDNA transfected HeLa cells or in reticulocyte lysates containing canine pancreatic membranes, band A is modified by glycosylation to yield a version of apparent molecular weight 135 kd called band B. The use of polyclonal and monoclonal antibodies to CFTR showed that non-recombinant T84 cells contain, in addition, a diffusely migrating 150 kd (band C) version of CFTR.

CFTR from T84 Cells

CFTR can be detected in T84 cells by adding ($\gamma$32P) ATP and protein kinase A to immunoprecippitates formed using antibodies raised against CFTR (see Gregory et al., 1990 above). Band B, and large amounts of band C were detected by this method (see FIG. 1). Partial proteolysis fingerprinting showed that the T84 cell derived material and that produced in a cell-free system directed by CFTR RNA were indistinguishable.

FIG. 1 demonstrates that band C is CFTR modified by addition of N-linked carbohydrate. Upon treatment with N-GLYCANASE® enzyme, band C, immunoprecipated from T84 cells and phosphorylated in vitro is converted to band A. Treatment with O-GLYCANASE® enzyme, endoglycosidase H or endoglycosidase F enzymes had no effect (FIG. 1). Because a band of intermediate molecular weight was also detected upon treatment with N-GLYCANASE® enzyme, these results can be interpreted to mean that CFTR bears two complex carbohydrate side chains possibly of the tri-or tetra-antennary type. N-GLYCANASE® enzyme treatment of band B also yielded band A (FIG. 9) (Gregory et al., 1990 above). The shift in apparent molecular weight on polyacrylamide gels in going from band A to band C seems large (20K) but whether this represents addition of unusually larged side chains, or merely results from anomalous migration in SDS-polycrylamide gels is unknown. It is postulated that glycosylation of band C is probably also responsible for its migration as a diffuse band as opposed to the sharp appearance of bands A and B.

Intracellular Characterization of CFTR

Based on the discoveries of this invention, nascent CFTR interacts first with the endoplasmic reticulum and is then glycosylated at at least one of Asn residues 894 and 900. The native molecule is then transported to the Golgi where carbohydrate processing to complex-type glycosylation occurs. Finally, at least some of the mature glycosylated molecule is thereafter transported to the plasma membrane. It is now reasonably well established that the endoplasmic reticulum possesses a mechanism that prevents transport of mutant, misfolded or incorrectly complexed versions of proteins otherwise destined for further processing.

SUMMARY OF THE INVENTION

The present invention provides a method for purifying a membrane associated protein, e.g., cystic fibrosis transmembrane conductance regulator (hereinafter CFTR), in a functional form. The method involves contacting a membrane-associated protein-membrane fraction complex with a detergent forming a solubilized complex and chromatographically isolating the membrane-associated protein from the solubilized complex in a functional form. The functional form of the purified membrane-associated protein of the present invention preferably is sufficiently pure to allow its introduction into humans for therapeutic purposes.

DETAILED DESCRIPTION

Figure 1:
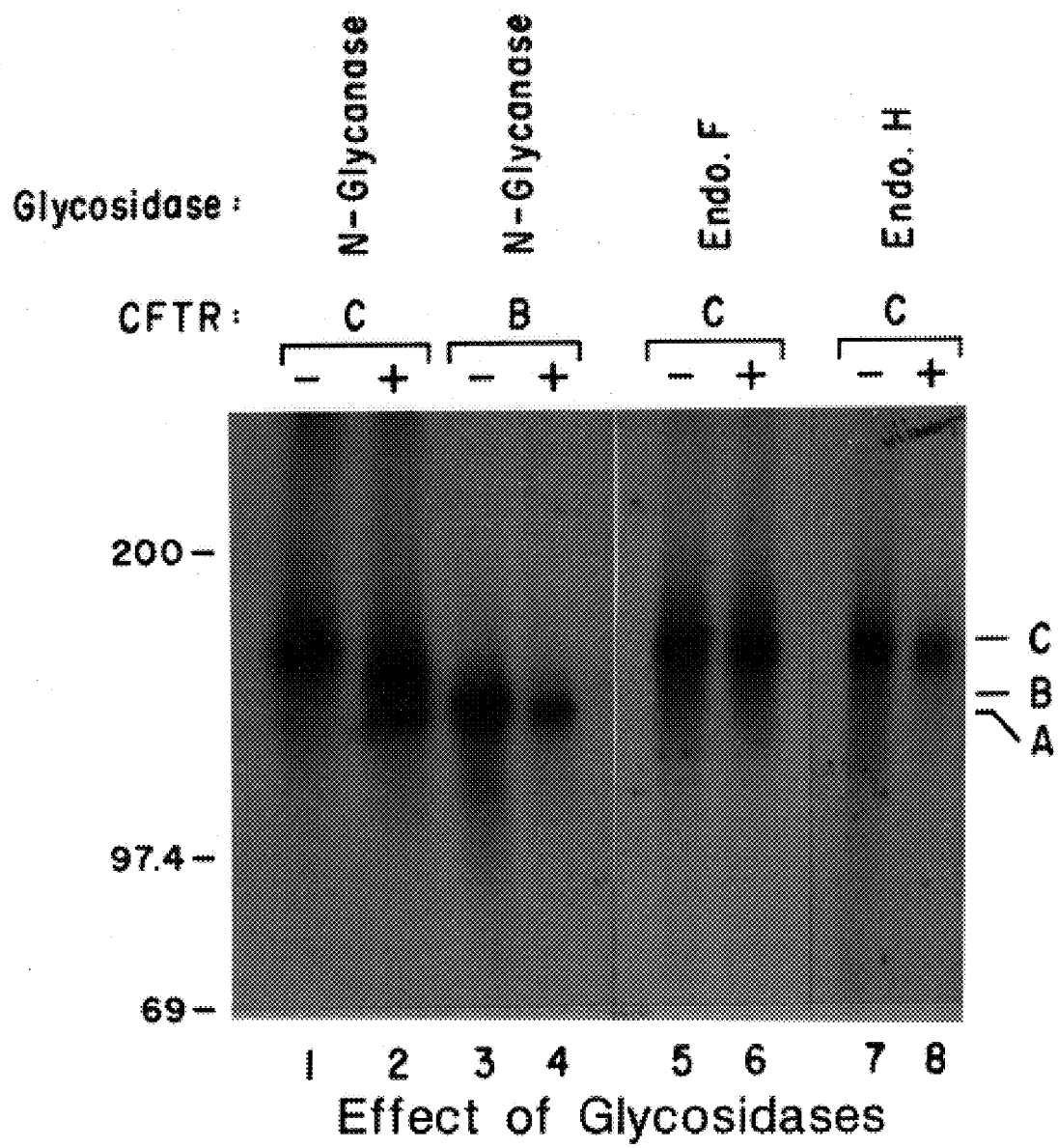
FIG. 1 demonstrates different patterns of glycosylation for CFTR.

The present invention pertains to a method involving contacting a membrane-associated protein-membrane fraction complex with a detergent forming a solubilized complex and chromatographically isolating the membrane-associated protein from the solubilized complex in a functional form.

The language "membrane-associated protein" is intended to include transmembrane proteins, peripheral membrane proteins, and integral membrane proteins. Transmembrane proteins extend across the membrane. Peripheral membrane proteins are bound to one or the other face of the membrane generally through interactions with, for example, other membrane-associated proteins. Peripheral membrane proteins can also be associated with the membrane by attachment to a fatty acid chain inserted into the membrane or by attachment to an oligosaccharide which is in turn attached to a fatty acid chain inserted into the membrane. Integral membrane proteins are generally transmembrane proteins linked to a fatty acid chain in the membrane. Examples of transmembrane proteins include ion channels, particularly chloride ion channels such as cystic fibrosis transmembrane conductance regulator (CFTR).

The language "detergent" is intended to include surface active agents capable of forming solubilized complexes of the membrane-associated protein-membrane fraction complex. Several different criteria are used for choosing a detergent suitable for solubilizing the complex. For example, one property considered is the ability of the detergent to solubilize the CFTR within the membrane fraction at minimal denaturation of the membrane-associated protein allowing for the activity or functionality of the membrane-associated protein to return upon reconstitution of the protein. Another property considered when selecting the detergent is the critical micells concentration (CMC) of the detergent in that the detergent of choice preferably has a high CMC value allowing for ease of removal after reconstitution. A third property considered when selecting a detergent is the hydrophobicity of the detergent. Typically, membrane-associated proteins are very hydrophobic and therefore detergents which are also hydrophobic, e.g. the triton series, would be useful for solubilizing the hydrophobic proteins. Another property important to a detergent can be the capability of the detergent to remove the CFTR with minimal protein-protein interaction facilitating further purification. A fifth property of the detergent which is considered is the charge of the detergent. For example, if it is desired to use ion exchange resins in the purification process, then the preferable detergent would be an uncharged detergent. Examples of detergents which are useful within the present invention include CHAPS and CHAPSO (preferably in the presence of 0.5M NaCl), Digitonin, Octylglucoside, HECAMEG, Triton X-100 and Triton X-114, sodium cholate, dodecylmaltoside, sucrose monolaurate, Deoxy BIG-CHAP, α-lyso Phosphatidylcholine (α-lyso PC), α-lyso Palmitoyl Phosphatidylcholine (α-lyso PPC), and α-lyso myristoyl Phosphatidylcholine. The preferred detergent of the present invention for CFTR is α-lyso PC which solubilizes 80 percent CFTR from the membrane fraction and approximately 50 percent total cell protein. It should be understood that the solubilization effect of the detergent can be increased or adjusted by adjusting other parameters, e.g., increasing the salt concentration.

References that describe use of phosphatidylcholine detergents include P. Jezek, et al., *Journal of Biological Chemistry*, 265, 1990, pp. 10522–10526; J. Zhang, et al., *Journal of Biological Chemistry*, 267, 1992, pp. 9773–9778; S. Dunn, et al., *Biochemistry*, 28, 1989, pp. 2545–2551; and C. Mundina-Weilenmann, et al., *Journal of Biological Chemistry*, 266, 1991, pp. 4067–4073.

The language "forming a solubilized complex" is intended to include complexes wherein the membrane-associated protein is not entirely embedded in the membrane fraction and is solubilized at least to an extent which allows it to be chromatographically isolated from the membrane fraction. The membrane-associated protein can be completely solubilized or separated from the membrane fraction complex but does not have to be completely separated and can be separated to the extent sufficient to allow chromatographic isolation.

The language "membrane fraction" is intended to include the portion of the membrane in association with the membrane-associated protein after lysis. The membrane fraction includes the membrane vesicle.

The language "chromatographically isolating" is intended to include techniques capable of isolating the membrane-associated protein based upon principles of chromatography. Examples of types of such art-recognized chromatographic techniques include hydrophobic interaction, lectin affinity, ion exchange, dye affinity and immunoaffinity. Examples of materials used within hydrophobic interaction chromatographic techniques include phenyl sepharose, butyl sepharose and artificial membrane technology. An example of a material used in a lectin affinity chromatographic technique is wheat germ agglutin sepharose. The protein being separated in the lectin affinity chromatographic technique can be eluted from the material using N-acetyl glucosamine. Examples of materials used in ion-exchange chromatographic techniques include S-sepharose, Q-sepharose, DEAE-sepharose and CM-sepharose. Examples of materials used in dye affinity techniques include resins selected from the group consisting of basilene blue dye, piski dye and green dye. Examples of materials used in an immunoaffinity chromatographic technique include monoclonal antibodies.

The language "monoclonal antibody" is art-recognized terminology. The monoclonal antibodies of the present invention can be prepared using classical cloning and cell fusion techniques. The immunogen (antigen) of interest, e.g., different portions of CFTR, is typically administered (e.g., intraperitoneal injection) to mice or rabbits as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin. In these cases, the peptides serve as haptens with the carrier proteins. After the mouse or rabbit is boosted, for example, three or four times, the spleen is removed and splenocytes are extracted and fused with myeloma cells using the well-known processes of Kohler and Milstein (*Nature* 256: 495–497 (1975)) and Harlow and Lane (Antibodies: A Laboratory Manual, Cold Spring Harbor Laboratory, New York, 1988). The resulting hybrid cells are then cloned in the conventional manner, e.g., using limiting dilution, and the resulting clones, which produce the desired monoclonal antibodies, cultured.

Examples of monoclonal antibodies raised againt human CFTR using this method include mAb 13-1, mAb 13-2, mAb 24-1, and mAb 24.2. The monoclonal antibodies mAb 13-1 and mAb 13-2 recognize amino acids found in exon 13. MAb 13-1, for example, recognizes amino acids 729–736 of human CFTR and is produced by the hybridoma deposited under American Type Culture Collection (ATCC) Accession No. ATCC HB 10565. MAb 13-2 is produced by the hybridoma deposited under ATCC Accession No. HB 10566. MAb 24-1 recognizes amino acids 1477–1480 of human CFTR and is produced by the hybridoma deposited under ATCC Accession No. ATCC HB 11947. MAb 24-2 recognizes amino acids 1433–1439 of human CFTR and is produced by the hybridoma deposited under ATCC Accession No. ATCC HB 11946.

Mab 13-1 (deposited with the American Type Culture Collection, as ATCC HB 10565) is directed to the R-domain of CFTR, and mAb 24-1 (also deposited with the American Type Culture Collection as ATCC HB 11947) is directed towards the C-terminus of CFTR. These monoclonal antibodies were previously described in a co-pending application cited above.

In support of this Patent, and pursuant to 37 CFR 1.808, all restrictions imposed by the depositor on the availability to the public of the below-listed deposits are irrevocably removed as of the issue date of this Patent.

(1) ATCC designation, HB11947, hybridoma mAb 24-1, deposited Jun. 16, 1995
(2) ATCC designation, HB 10565, hybridoma mAb 13-1, deposited Sep. 27, 1990. The address of the ATCC is 12301 Parklawn Drive, Rockville, Md. 20852.

The purification process of the present invention can also contain optional steps such as gel filtration step subsequent to the chromatographic isolation step and a stripping step prior to the contacting step. Gel filtration is art recognized and an example of a material which can be used in the gel filtration step is superdex 200 HR 10/30 (Pharmacia) as described in the examples below. The alkali stripping step is also described in detail in the examples set forth below.

The present invention also pertains to purified membrane associated proteins produced by the methods of the present invention. The purified membrane-associated proteins preferably are sufficiently pure to allow their introduction into mammals, especially humans. This language is intended to include a level selected by the appropriate regulatory agency for the use of the membrane-associated protein and the various steps of the methods of the present invention can be varied to achieve the desired or required purity. For example, the FDA can require at least a 90 percent purity on some human injectables. The purified membrane-associated protein product of the present invention preferably has a purity of at least about 50 percent, more preferably at least about 70 percent and most preferably at least about 80 percent.

It should be understood that various combinations of the chromatographic material and detergent may be desired for a particular membrane-associated protein or a particular detergent may be preferable when using a particular chromatographic material. Examples of some useful combinations are set forth in Table 1 below.

TABLE 1

| Membrane-Associated Protein | Chromatographic Material | Detergent |
| --- | --- | --- |
| A) CFTR | S-Sepharose (Pharmacia) | CHAPSO Lyso-PC |
| B) CFTR | Q-Sepharose (Pharmacia) | Lyso PC Mega sucrose monolaurate deoxy BIG-CHAP |
| C) CFTR | DEAE-Sepharose (Pharmacia) | Lyso-PC |
| D) CFTR | CM-Sepharose (Pharmacia) | Sucrose monolaurate |
| E) CFTR | Phenyl-Sepharose (Pharmacia) | Triton X-100 |
| F) CFTR | Phenyl-Sepharose (ISS) | SDS |
| G) CFTR | Butyl-Sepharose (Pharmacia) | CHAPSO |
| H) CFTR | Mimetic Column-IAM Chromatography (Regis Chemicals) | CHAPSO Triton X-100 |
| I) CFTR | Basilene Blue Resin | CHAPSO |
| J) CFTR | Piksi Dye Affinity Resin (ISS) | Triton X-100 |
| K) CFTR | Green Dye Resin | Triton X-100 |
| L) CFTR | Wheat Germ Lectin (Pharmacia) | CHAPSO |

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example 1

Purification of CFTR from CHO-CFTR Cells Using α-lyso Phosphatidyleholine and A Monoclonal Antibody 13-1 Immunoaffinity Resin Preparation of the Membrane Fractions CHO cells stably expressing CFTR (hereinafter CHO CFTR cells) were prepared and pelleted as described previously (Tilly et al. (1992) *The Journal of Biological Chemistry*, Vol. 267, No. 14, pp. 9470–73; Anderson et al. (1991) *Science*, 251, pp. 679–682). The CHO CFTR cells were grown in spinners (8L) on DE52 microcarriers (sold by Pharmacia). The cells were pelleted from the cell culture by centrifuging (1000xg) for five minutes. The cell pellets were washed twice with phosphate buffered saline (PBS) and the wash solution was discarded. The pellets were resuspended in a hypotonic lysis buffer (10 mM NaCl, 20 mM Tris HCl, 1 mM EDTA, 2 mM MgCl$_2$) on ice for thirty minutes. Protease inhibitors included with the hypotonic lysis buffer were as follows: DTT (5 mM), benzamidine (10 mM), PMSF (0.5 mM), leupeptin (1 uM), Pepstatin A (1 uM) and Aprotinin (20 ug/ml). The suspension was passed through a microfluidizer at 2000–3000 psi and centrifuged (1000 xg) for ten minutes. The supernatant was separated and centrifuged (10,000 xg) for an additional twenty-five minutes. Again, the supernatant was separated and centrifuged (100,000 xg) for one hour. The final pellet was the crude membrane fraction containing the CFTR (hereinafter the CFTR-membrane fraction complex). The CFTR-membrane fraction complex was resuspended in a solution (150 mM NaCl, 50 mM Tris HCl, 1 mM EDTA, 10% glycerol (pH 7.5)) and then subjected to the stripping process described below.

Alkali Stripping of CFTR-Membrane Fraction Complex

The alkali stripping is an optional step which removes the peripherally bound membrane proteins from the complex. The resulting complex is enriched for CFTR as this procedure removes a large percentage of total membrane protein, e.g. 60 percent, but does not remove the CFTR or membrane-associated protein.

The CFTR-membrane fraction complex was diluted with ten volumes of 10 mM EDTA (pH 10.0) and allowed to sit on ice for two minutes. The stripped complex was collected via centrifugation (100,000 xg) of the diluted solution for approximately sixty minutes forming a stripped CFTR-membrane fraction complex.

Solubilization of the Stripped CFTR-Membrane Fraction Complex and Purification of CFTR from the Solubilized Complex Using MAb 13-1 Immunoaffinity Resin: Peptide Elution The stripped complex was diluted (4 mg/ml) in a solubilization buffer (150 mM KCl; 50 mM Tris HCl; 1 mM EDTA; 10% glycerol; 1.5% α-lyso PC (pH 7.5)) and rotated for one hour at 4° C. Subsequently, the solution was centrifuged at 4° C. for one hour at 100,000 xg (40,000 rpm in A641 rotor). The supernatant was saved and rocked with approximately 15 mls. of MAb 13-1 hydrazide resin overnight at 4° C. in a batch process. The resin was washed with 100 mls of a wash buffer (150 mM NaCl; 50 mM Tris HCl; 1 mM EDTA, 1% Cholate (pH 8.0)) also in a batch process. The resin was gently resuspended in a column with 10 mls of elution buffer (150 mM KCl; 50 mM Tris HCl; 1 mM EDTA; 10% glycerol; 5 mM peptide for MAb 13-1: SDEPLERRLS-NH$_2$ MW=1189.9; 0.5% cholate. Immediately before use 1 mM Pefabloc, Aprotinin 20 ug/ml, 10 mM benzamidine, 5 ug/ml Pepstatin A, 5 ug/ml Leupeptin was added) and rocked for thirty minutes to equilibrate. The resin column was completely drained and the fraction was collected. This process was repeated four times using ten to fifteen minute incubations each time collecting the fractions. The column was washed with approximately 50 mls of storage buffer (150 mM NaCl, 25 mM Tris HCl, 1 mM EDTA and 0.02% NaN3) and stored at 4° C. The collected fractions containing immunoaffinity purified CFTR (approximately 50 percent pure) were pooled and concentrated to 500 ul using a Centricell concentrating device. An aliquot (200 ul) of this concentrate was applied to a Superdex resin and the purified CFTR collected from the Superdex resin was approximately 80 percent pure. Approximately 300 mgs of the CFTR-membrane fraction complex yielded approximately 1 mg of 80 percent pure CFTR.

Example 2

Purification of CFTR from CHO-CFTR Cells Using α-lyso Phosphatidylcholine and A Monoclonal Antibody 24-1 Immunoaffinity Resin This example was conducted as described in Example 1 above with the exception that a MAb 24-1 hydrazide resin was used in place of the MAb 13-1 hydrazide resin and 5 mM peptide for MAb 24-1: VQDTRL MW: 726.8 was used in the elution buffer in place of the peptide for MAb 13-1. The final CFTR production was 50 percent pure and the yield was similar to that described in Example 1.

Example 3

Purification of CFTR from CHO-CFTR Cells Using α-lyso Phosphatidylcholine and A Monoclonal Antibody 13-1 Immunoaffinity Resin and High pH Elution This example is conducted as described in Example 1 above with the exception that a high pH elution buffer (150 mM NaOH, 10% glycerol, 0.5% Cholate (pH 11.0)) is used in the immunoaffinity purifiacation step. The column is eluted at 1 ml/minute and the fractions (5 ml) are collected. The fractions are immediately neutralized by adding 1 M Tris HCl (250 ul) to the collection tubes prior to collecting the fractions (final concentration=50 mM). The neutralized fractions are further purified as described in Example 1.

Example 4

Purification of CFTR from CHO-CFTR Cells Using α-lyso Phosphatidylcholine and a Monoclonal Antibody 24-1 Immunoaffinity Resin and High pH Elution This example is conducted as described in Example 2 above with the exception that a high pH elution buffer (150 mM NaOH, 10% glycerol, 0.5% Cholate (pH 11.0)) is used in the immunoaffinity purification step. The column is eluted at 1 ml/minute and the fractions (5 ml) are collected. The fractions are immediately neutralized by adding 1 M Tris HCl (250 ul) to the collection tubes prior to collecting the fractions (final concentration=50 mM). The neutralized fractions are further purified as described in Example 2.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A method of purifying cystic fibrosis transmembrane conductance regulator (CFTR) protein having complex-type glycosylation from a mammalian cell comprising the steps of:

(A) providing a mammalian cell membrane fraction with which said complex-type glycosylated CFTR is an integral membrane protein;

(B) alkali-stripping at least about 60% of peripherally bound membrane protein from said fraction;

(C) contacting said stripped membrane fraction with a buffered solution containing alpha lysophosphatidylcholine detergent in order to solubilize at least about 80% of CFTR from the membrane fractions without solubilizing more than 50% of non-CFTR protein molecules;

(D) contacting solubilized CFTR with anti-CFTR monoclonal antibody in the presence of a concentration of alpha lysophosphatidylcholine detergent that permits specific interaction of CFTR to the antibody; and (E) dissociating said antibody-CFTR complex in the presence of cholate detergent.

2. The method of claim 1, wherein the buffered solution in step (c) contains 1.5% alpha lysophosphatidylcholine detergent, 150 mM KCl, 50 mM Tris HCl, 1 mM EDTA, and 10% glycerol at pH 7.5.

3. The method of claim 1, wherein the antibody in step (D) is mAb 13-1 or mAb 24-1.

4. A method of purifying cystic fibrosis transmembrane conductance regulator (CFTR) protein having complex-type glycosylation from a mammalian cell comprising the steps of:

(A) providing a mammalian cell membrane fraction with which said complex-type glycosylated CFTR is an intergral membrane protein;

(B) alkali-stripping at least about 60% of peripherally bound membrane protein from said fraction;

(C) contacting said stripped membrane fraction with a solution containing 1.5% alpha lysophosphatidylcholine detergent, 150 mM KCl, 50 mM Tris HCl, 1 mM EDTA, and 10% glycerol at pH 7.5 for 1 hour at 4° C. in order to solubilize at least about 80% of CFTR from the membrane fractions without solubilizing more than 50% of non-CFTR protein molecules;

(D) contacting solubilized CFTR with anti-CFTR monoclonal antibody mAb 13-1 or mAb 24-1 in the presence of a concentration of alpha lysophosphatidylcholine detergent that permits specific interaction of CFTR to the antibody; and (E) disociating said antibody-CFTR complex in the presence of cholate detergent.

* * * * *